(12) United States Patent
Shia et al.

(10) Patent No.: US 7,713,246 B2
(45) Date of Patent: May 11, 2010

(54) AUTOMATIC VALVE

(75) Inventors: Benedict Shia, Needham, MA (US); Rork Swisher, St. Charles, MO (US); James Hanlon, Manchester, MO (US); Glenn Fournie, Smithton, IL (US); Robert Coon, Chicago, IL (US); Gary Prokop, Wheaton, IL (US); James Hand, Glen Ellyn, IL (US); Joey Nakayama, Chicago, IL (US); Daniel Peterson, Chicago, IL (US)

(73) Assignee: Covidien AG (CH)

( * ) Notice: Subject to any disclaimer, the term of this patent is extended or adjusted under 35 U.S.C. 154(b) by 634 days.

(21) Appl. No.: 10/532,392

(22) PCT Filed: Oct. 28, 2003

(86) PCT No.: PCT/US03/34129

§ 371 (c)(1),
(2), (4) Date: Aug. 5, 2005

(87) PCT Pub. No.: WO2004/039286

PCT Pub. Date: May 13, 2004

(65) Prior Publication Data

US 2006/0122559 A1 Jun. 8, 2006

Related U.S. Application Data

(63) Continuation-in-part of application No. 10/281,638, filed on Oct. 28, 2002, now Pat. No. 7,097,632.

(51) Int. Cl.
*A61M 5/00* (2006.01)

(52) U.S. Cl. .................................................. 604/249

(58) Field of Classification Search ................. 604/533, 604/246, 249, 167.01, 167.05
See application file for complete search history.

(56) References Cited

U.S. PATENT DOCUMENTS 2,335,085 A 11/1943 Roberts (Continued)

FOREIGN PATENT DOCUMENTS

DE 9201574 U1 4/1992

(Continued)

OTHER PUBLICATIONS

Non-Final Office Action issued in U.S. Appl. No. 11/286,094, dated Apr. 16, 2008, 7 pages.

(Continued)

*Primary Examiner*—Kevin C Sirmons
*Assistant Examiner*—Elizabeth R Moulton
(74) *Attorney, Agent, or Firm*—Edward S. Jarmolowicz, Esq.

(57) ABSTRACT

A valve system is provided having a housing including a first end, a second end and a first passageway. The housing has a first port and a second port. A valve member is disposed within the housing and movable relative thereto. The valve member defines a portion of the first passageway that includes a first opening configured for alignment and sealed fluid communication with the first port and the second port. The portion of the first passageway further includes a second opening having a greater relative dimension than the first opening. The valve member is manipulable to establish sealed fluid communication between the first opening and the first port or the second port while maintaining continuous sealed fluid communication between the second opening and the first passageway adjacent to the second end of the housing. The valve member can be disposed within the housing for rotation relative thereto.

26 Claims, 7 Drawing Sheets

U.S. PATENT DOCUMENTS

| | | | |
|---|---|---|---|
| 2,452,643 A | 11/1948 | Fields | |
| 2,510,125 A | 6/1950 | Meakin | |
| 3,148,895 A | 9/1964 | Jasper et al. | |
| 3,469,863 A | 9/1969 | Riester et al. | |
| 3,860,000 A | 1/1975 | Wootten et al. | |
| 3,889,675 A | 6/1975 | Stewart | |
| 3,957,082 A * | 5/1976 | Fuson et al. | 604/248 |
| 4,082,095 A | 4/1978 | Mendelson et al. | |
| 4,112,932 A | 9/1978 | Chiulli | |
| 4,162,092 A | 7/1979 | Hayes | |
| 4,236,515 A | 12/1980 | Genese | |
| 4,237,880 A | 12/1980 | Genese | |
| 4,258,717 A | 3/1981 | Bisera et al. | |
| 4,269,219 A | 5/1981 | Dybvig | |
| 4,478,436 A | 10/1984 | Hashimoto | |
| 4,573,965 A | 3/1986 | Russo | |
| 4,617,012 A | 10/1986 | Vaillancourt | |
| 4,653,542 A | 3/1987 | Tascher | |
| 4,696,671 A | 9/1987 | Epstein et al. | |
| 4,729,401 A | 3/1988 | Raines | |
| 4,735,607 A | 4/1988 | Keith, Jr. | |
| 4,754,993 A | 7/1988 | Kraynick | |
| 4,790,832 A | 12/1988 | Lopez | |
| 4,838,856 A | 6/1989 | Mulreany et al. | |
| 4,865,584 A | 9/1989 | Epstein et al. | |
| 4,895,562 A | 1/1990 | Lopez | |
| 4,900,065 A | 2/1990 | Houck | |
| 4,941,875 A | 7/1990 | Brennan | |
| 4,994,048 A | 2/1991 | Metzger | |
| 5,057,093 A | 10/1991 | Clegg et al. | |
| 5,069,661 A | 12/1991 | Trudell | |
| 5,088,486 A * | 2/1992 | Jinotti | 128/207.14 |
| 5,217,432 A | 6/1993 | Rudzena et al. | |
| 5,234,417 A | 8/1993 | Parks et al. | |
| 5,250,041 A | 10/1993 | Folden et al. | |
| 5,256,160 A | 10/1993 | Clement | |
| 5,261,459 A * | 11/1993 | Atkinson et al. | 137/846 |
| 5,263,945 A | 11/1993 | Byrnes et al. | |
| 5,267,983 A | 12/1993 | Oilschlager et al. | |
| 5,273,523 A | 12/1993 | Sozuki et al. | |
| 5,309,902 A * | 5/1994 | Kee et al. | 128/202.27 |
| 5,322,073 A | 6/1994 | Michels et al. | |
| 5,328,478 A | 7/1994 | McVay | |
| 5,395,352 A | 3/1995 | Penny | |
| 5,399,173 A | 3/1995 | Parks et al. | |
| 5,403,280 A | 4/1995 | Wang | |
| 5,403,290 A | 4/1995 | Noble | |
| 5,417,664 A | 5/1995 | Felix et al. | |
| 5,429,485 A | 7/1995 | Dodge | |
| 5,531,723 A | 7/1996 | Solazzo | |
| 5,535,771 A | 7/1996 | Purdy et al. | |
| 5,536,258 A | 7/1996 | Folden | |
| 5,540,668 A | 7/1996 | Wilson et al. | |
| 5,549,657 A | 8/1996 | Stern et al. | |
| 5,556,137 A | 9/1996 | Ream | |
| 5,558,371 A | 9/1996 | Lordo | |
| 5,620,427 A | 4/1997 | Werschmidt et al. | |
| 5,702,363 A | 12/1997 | Flaherty | |
| 5,738,648 A | 4/1998 | Lands et al. | |
| 5,741,003 A * | 4/1998 | Segien, Jr. | 251/95 |
| 5,776,117 A | 7/1998 | Haselhorst et al. | |
| 5,836,909 A | 11/1998 | Cosmescu | |
| 5,848,814 A | 12/1998 | Nadasky et al. | |
| 5,988,700 A | 11/1999 | Prichard | |
| 6,165,168 A | 12/2000 | Russo | |
| 6,270,478 B1 | 8/2001 | Mernoe | |
| 6,309,370 B1 | 10/2001 | Haim et al. | |
| 6,332,467 B1 | 12/2001 | Hutson et al. | |
| 6,399,173 B1 | 6/2002 | Nagayama et al. | |
| 6,461,335 B1 | 10/2002 | Noecker | |
| 6,551,270 B1 | 4/2003 | Bimbo et al. | |
| 6,808,521 B1 | 10/2004 | McMichael | |
| 6,851,448 B2 | 2/2005 | Fujii | |
| 6,893,056 B2 | 5/2005 | Guala | |
| 7,128,348 B2 | 10/2006 | Kawamura et al. | |
| 2003/0009152 A1 | 1/2003 | O'Hara et al. | |
| 2003/0116961 A1 | 6/2003 | Patterson | |
| 2003/0153897 A1 | 8/2003 | Russo | |
| 2003/0191445 A1 | 10/2003 | Wallen et al. | |
| 2003/0195478 A1 | 10/2003 | Russo | |
| 2003/0209681 A1 | 11/2003 | Leinsing et al. | |
| 2003/0236500 A1 | 12/2003 | Scheu | |
| 2004/0186457 A1 | 9/2004 | Truitt et al. | |
| 2004/0201216 A1 | 10/2004 | Segal et al. | |
| 2005/0027282 A1 | 2/2005 | Schweikert et al. | |
| 2005/0033269 A1 | 2/2005 | Decaria | |
| 2005/0171468 A1 | 8/2005 | Wood | |
| 2005/0245899 A1 | 11/2005 | Swisher | |

FOREIGN PATENT DOCUMENTS

| | | |
|---|---|---|
| DE | 198 19 432 | 11/1999 |
| EP | 0151519 A1 | 8/1985 |
| EP | 0633039 B1 | 10/2004 |
| EP | 1 234 596 B1 | 1/2007 |
| GB | 1262146 | 2/1972 |
| JP | 10234863 A | 9/1998 |
| JP | 2002017871 A | 1/2002 |
| JP | 2002035140 A | 2/2002 |

OTHER PUBLICATIONS

USPTO Office action issued in U.S. Appl. No. 12/059,468 dated Oct. 29, 2008, 7 pages.

USPTO Office action issued in U.S. Appl. No. 11/286,094 dated Oct. 29, 2008, 9 pages.

Office Action dated Feb. 12, 2009 from related U.S. Appl. No. 11/286,904, 11 pages.

Office Action dated Apr. 20, 2009 from related U.S. Appl. No. 12/059,468, 9 pages.

* cited by examiner

AUTOMATIC VALVE

RELATED APPLICATION INFORMATION

This patent application is a continuation-in-part of U.S. application Ser. No. 10/281,638 filed on Oct. 28, 2002 now U.S. Pat. No. 7,097,632 by Shia et al., the entire contents of which is incorporated herein by reference.

BACKGROUND

1. Technical Field

The present disclosure generally relates to medical administration of fluids with a subject, and more particularly, to a valve system, having multiple ports, which is manipulated to establish fluid communication with a passageway of a nasogastric tube.

2. Description of the Related Art

Medical systems inserted with a body of a subject for the administration of fluids with the subject, such as, for example, nasogastric tubing are known in the art. Nasogastric tubing is typically employed in hospitals, nursing homes, care facilities, etc. to remove fluids from the body of the subject, such as, for aspirating fluids from a gastrointestinal tract (GI tract) of the subject or to introduce nutrients, supplements, medicines, etc. to the subject.

In one application, nasogastric tubing aspirates fluid and air to decompress the contents of the subject's stomach to avoid damaging the inner wall, e.g., the gastric mucosa. Nasogastric tubing may also facilitate removal of accumulated fluids, blood, etc. from the GI tract due to disease, intestinal obstruction, bleeding ulcers and paralytic ulcers to prevent progressive distension of the GI tract. Progressive distension of the GI tract can lead to shock, visceral injury and vomiting. Vomit may be aspirated into the respiratory tract and cause asphyxia and pneumonia.

Nasogastric tubes are employed with subjects undergoing abdominal surgery to keep the stomach vacant of fluid and postoperatively to prevent complications, such as, decreased gastrointestinal function. Such nasogastric tubing advantageously prevents pooling of liquids in the GI tract to facilitate postoperative recovery of digestive function. Nasogastric tubing can also be employed to protect gastric suture lines, preventing and treating paralytic ileus, treating drug overdoses, lavage, as well as other conditions that affect the GI tract.

In conventional use, a flexible plastic nasogastric tube is employed. The nasogastric tube defines a passageway that extends from a proximal end to a distal end. A practitioner introduces the distal end of the nasogastric tube through a nasal canal of a subject via one of the nostrils. The distal end is passed through the pharynx and down the esophagus into the GI tract. The distal end can be passed into the duodenum, stomach, etc. depending on the particular application such as, for example, aspirating fluids, introduction for medication, feeding, etc. Several openings are formed in the distal end that permit passage of gastric fluids, nutrients, medication, etc.

To prevent blockage of the openings in the distal end, a dual lumen nasogastric tube is generally used. The dual lumen nasogastric tube includes a suction/irrigation lumen and a separate vent lumen. The suction/irrigation lumen is connected to a suction source providing either intermittent or continuous suction to facilitate suction drainage and irrigation. The vent lumen communicates with the suction/irrigation lumen adjacent the distal end of the nasogastric tubing to permit atmospheric air to be drawn through the vent lumen into the suction lumen. The flow of atmospheric air moderates the amount of suction and flow during aspiration. Nutrients or medication introduced is passed down the suction lumen and the vent lumen is clamped or plugged. Air pressure is applied thereafter to clear the vent lumen.

The proximal end of the nasogastric tube exits the nostril and communicates with a suction source. The proximal end may be connected to the suction source, a feeding pump, etc. through a connector that may communicate with a collection vessel. In a fluid aspirating application, stomach fluids are drawn through the openings in the distal end, through the passageway and into the collection vessel, as facilitated by the suction source. In a fluid introduction application, nutrients, medication, etc. are injected into the passageway and forced through the openings in the distal end and into for example, the duodenum.

The connector is connected to a second tube that is connected to the suction source, or alternatively, to a feeding pump. Frequently, the nasogastric tubing must be alternated to a source for suction, feeding or introduction of an injection. To alternate the nasogastric tubing application, the second tube is removed from the connector or the connector is removed from the proximal end of the nasogastric tubing and the desired connection is made. These known devices and methods suffer from many drawbacks. Typically, the practitioner is spattered with vomit or other fluid during disconnection of the tubing and connector.

This procedure may also require clamping of the tubing. This is disadvantageously cumbersome, unclean and does not adequately prevent leakage of GI tract fluids. Leaking and splattering intestinal fluids can cause contamination of wounds, tubing and catheters. The intestinal fluids may contain infectious material that poses serious health risks to the practitioner.

Another drawback of these devices and methods is the labor intensive burden of cleaning the leaking and splattering intestinal fluids. Patient discomfort and complication may also result. This consumes a great deal of practitioner time and adds to the cost of healthcare.

Therefore, it would be desirable to overcome the disadvantages and drawbacks of the prior art with a valve system, having multiple ports, which is manipulated to establish fluid communication with a passageway of a nasogastric tube to avoid leakage of intestinal fluids and minimize disease propagation. It would be desirable if such a valve system included a rotatable valve member that is manipulated to facilitate connection of the passageway of the nasogastric tube with alternate sources to achieve the principles of the present disclosure. It would be highly desirable if the valve system is connected to a second passageway of the nasogastric tube. It is contemplated that the valve system and its constituent parts are easily and efficiently manufactured and assembled.

SUMMARY

Accordingly, a valve system, having multiple ports, is provided that is manipulated to establish fluid communication with a passageway of a nasogastric tube to avoid leakage of intestinal fluids and minimize disease propagation to overcome the disadvantages and drawbacks of the prior art. Desirably, such a valve system includes a rotatable cap that is manipulated to facilitate connection of the passageway of the nasogastric tube with alternate sources to achieve the principles of the present disclosure. Most desirably, the valve system is connected to a second passageway of the nasogastric tube. The valve system is easily and efficiently manufactured and, assembled. The present disclosure resolves related disadvantages and drawbacks experienced in the art.

In one particular embodiment, in accordance with the principles of the present disclosure, a valve system is provided including a valve connector that has a portion of a first passageway. The valve connector includes a suction port and an introduction port that are spaced apart and in substantially parallel alignment. The suction port and the introduction port are manipulable to establish fluid communication between the portion of the first passageway and the suction port or the introduction port. The valve connector may have a rotatable outer cap that includes the suction port and the introduction port. The cap is configured to facilitate manipulation of the suction port and the introduction port for establishing fluid communication with the portion of the first passageway.

The introduction port may include a normally closed valve. The normally closed valve can include an elastically deformable septum having an elongate slit formed through a thickness of the septum. The septum may be elastically deformable such that a cannula is engageable with the elongate slit to establish fluid communication between the cannula and the first passageway. The septum may be recessed relative to an outer surface of the valve connector. The valve connector may define a recessed cylindrical cavity, the cylindrical cavity including the septum. The septum may have an angular orientation relative to a longitudinal axis of the cylindrical cavity.

Alternatively, the valve connector defines a longitudinal axis and the portion of the first passageway defines an angled flow path. In another embodiment, the suction port and the insertion port are manipulable to establish fluid communication between the portion of the first passageway and the suction port and the insertion port.

The valve connector may be attached to a dual lumen nasogastric tube. In an alternate embodiment, the valve connector further includes a portion of a second passageway that includes a relief port. The relief port can include a one-way valve. The portion of the first passageway and a portion of the second passageway disposed within the valve connector fluidly communicate with the nasogastric tube. In another embodiment, the first passageway and the second passageway do not fluidly communicate within the valve connector.

In an alternate embodiment, a nasogastric valve system has a nasogastric tube including a first lumen and a second lumen. The first lumen defines a first portion of a first passageway. The second lumen defines a first portion of a second passageway. The first passageway and the second passageway fluidly communicate adjacent a distal end of the nasogastric tube. A valve connector having a first end and a second end are attached to the nasogastric tube. The valve connector includes a second portion of the first passageway and a second portion of the second passageway. The valve connector further includes a suction port and an introduction port that are spaced apart and in substantially parallel alignment. The suction port and the introduction port are manipulable to establish fluid communication between the second portion of the first passageway and the suction port or the introduction port. The introduction port defines a normally closed valve and the second portion of the second passageway defines a relief port.

In another alternate embodiment, the valve system has the portion of the first passageway and the portion of the second passageway being in fluid communication.

In yet another embodiment, a method for administration of fluids with a subject is provided. The method includes the steps of: providing a valve system, similar to those described; attaching a nasogastric tube, similar to those described, to the valve connector; inserting a distal end of the nasogastric tube into the subject via a passage of the subject; and manipulating a suction port and a introduction port of a valve connector of the valve system to establish fluid communication between a second portion of a first passageway of the nasogastric tube and the suction port or the introduction port.

The step of providing a valve system may further include a valve connector having a rotatable cap. The cap includes the suction port and the introduction port such that the step of manipulating includes rotating the cap to establish fluid communication with the suction port for removing fluid from the subject. Alternatively, the step of manipulating includes rotating the cap to establish fluid communication with the introduction port for injecting fluid with the subject.

In another alternate embodiment, a valve system is provided that includes a valve employed for nasogastric administration of patients that require suction, feeding, and medical irrigation due to temporary paralysis, decompression or obstruction of the gastrointestinal system. The valve is a single use hand held molded plastic assembly that is initially designed for use with double lumen nasogastric-sump tubes. The valve comprises an integral design that contains both an anti-reflux valve (ARV) mechanism to protect against biofluid contamination and a port selection mechanism that allows the user to medicate or irrigate without removal from feeding or suction lines. Other elements of the assembly include the incorporation of an introduction port that automatically closes and protects the user from fluid contamination and an anti-tamper mechanism that reduces the occurrence of accidental patient tampering.

The valve includes a similar top and bottom housing that are ultrasonically welded. These components offer an overall sleek design to the user. These components will generally be clear or lightly tinted to allow internal inspection of the device for clogs and foreign material. Inside of the welded body are three additional components that serve a variety of functions, including an ARV valve. The current design offers an additional feature of irrigation through the ARV valve. A knob is rotated by the user to select an open mode (for continuous suction or feeding), an off mode (for patient transportation) or a introduction mode (for medication and bolus feeding). The introduction port is used to ensure when the knob is rotated to the introduction mode, the flow path remains closed until an irrigation tip syringe is inserted through the introduction port. An enteral adapter is a soft PVC component that is bonded into a suction port on the bottom housing and allows securing of all enteral-feeding connectors to the suction port inner diameter without requiring an adapter.

In operation, a double lumen sump tube is first inserted through the nasal passage, down the esophagus and is positioned in the stomach. When placement is confirmed, a double barbed end of the valve is attached to the free end of the sump tube extending from the patient.

In normal operation, the knob is set to the "open" position to allow a fluid path from the sump tube to the suction/enteral adapter port. This setting allows suction through the main lumen. Alternatively, an enteral feeding connector can be attached to the suction port when continuous feeding is desired. When medication introduction is desired, the user will rotate the knob to the introduction port, insert an irrigation tip syringe through the introduction port and administer the medication through the main lumen. The introduction port includes a rubber component, to allow accommodation with a wide variety of irrigation tip syringes and contains a one-way bi-valve. This port allows passage of administered fluids to the patient but automatically closes upon removal of the syringe to check backflow of contaminating gastric fluids.

The knob can be rotated to the "off" mode in preparation for patient transportation. The off position is between the suction/feeding port and the introduction/medication port to close off the tube. Regardless of the knob position, the ARV is always operational.

The valve contains an anti-tamper mechanism that reduces the likelihood of patient tampering. The anti-tamper mechanism blocks the rotation of the knob and must be deactivated before the knob can be turned. The user first depresses and holds the central button while turning the knob. Alternatively, the anti-tamper mechanism is on the side and must be pressed towards the center of the connector and is held while the knob is turned.

The integral ARV prevents reflux from escaping out through the vent lumen. The one-way valve cannot be removed and thus will never be misplaced or lost. The irrigation tip port located above the ARV will allow the user to easily inject air into the vent lumen and establish the Pressure Activated Air Buffer (PAAB) in the lumen.

A dual port adapter is also included in the valve system and is a molded plastic part, aligned and bonded to the primary and secondary lumen of the sump tube. The dual port adapter connects the valve system. The valve is designed so that the user can remove it from the catheter for tube maintenance or connector replacement purposes. The dual port adapter facilitates connector changes that are straightforward, ergonomic and reliable.

The valve system of the present disclosure benefits from several advantages. The valve system integrates a 3-way valve and ARV into a hand held single use device. The integrated design reduces clutter and overall complexity of the system. The valve also contains fewer prominences and tabs that the current connector. This more sleek and continuous design presents less discomfort to the patient if he/she rolls onto the device.

Additionally, with the integrated ARV, this component cannot be lost. The valve system is reversible and generally requires only one-handed operation. Further, use of the device is intuitive due to simplified universal labeling and a transparent housing that readily shows the fluid flow path. The present valve system also prevents accidental suction at the same time the patient is medicating or irrigating.

The present valve system contains an anti-tamper mechanism that significantly reduces the incidence of inadvertent or deliberate tampering of the connector by the patient or non-clinical staff. The introduction port of the valve system contains a rubber seat that allows improved sealing to a wide variety of irrigation tip syringes.

In another embodiment, in accordance with the principles of the present disclosure, a valve system is provided having a housing including a first end, a second end and a first passageway that extends therealong. The housing further includes a first port and a second port. A valve member is disposed within the housing and movable relative thereto. The valve member defines a portion of the first passageway that includes a first opening configured for alignment and sealed fluid communication with the first port and the second port. The portion of the first passageway further includes a second opening having a greater relative dimension than the first opening. The valve member is manipulable to establish sealed fluid communication between the first opening and the first port or the second port while maintaining continuous sealed fluid communication between the second opening and the first passageway adjacent to the second end of the housing. The valve system may include a handle connected to the valve member to facilitate manipulation thereof.

The valve member can be disposed within the housing for rotation relative thereto to establish sealed fluid communication between the first opening and the first port or the second port. The valve member may be manipulable to a position such that the first opening is not aligned with the first port or the second port and fluid communication is prevented therebetween.

Alternatively, the first opening is releasably lockable in alignment with the first port and the second port. The housing may support a button that engages the valve member to release the first opening from alignment with the first port and the second port.

The housing may further include a third port, disposed adjacent the second end thereof, that fluidly communicates with the first passageway and connects to tubing that extends to the second opening and is supported thereby. The tubing is configured to facilitate fluid communication of the first passageway with the first port and the second port. The outer surface of the housing can provide visual indicia of a position of the first opening.

In an alternate embodiment, the housing includes an introduction port and a suction port, each being disposed adjacent the first end. The housing further includes an attachment port disposed adjacent the second end. The valve member is mounted for rotation within a cavity of the housing relative to a longitudinal axis thereof.

In another alternate embodiment, the housing includes a third port, disposed adjacent the second end, that fluidly communicates with the first passageway and connects to tubing. The tubing extends to the second opening and is supported thereby. The tubing is configured to facilitate fluid communication of the first passageway with the first port and the second port. The valve member is manipulable to establish sealed fluid communication between the first opening and the first port or the second port while maintaining continuous sealed fluid communication between the second opening and the third port via the tubing.

BRIEF DESCRIPTION OF THE DRAWINGS

The objects and features of the present disclosure, which are believed to be novel, are set forth with the particularity in the appended claims. The present disclosure, both as to its organization and manner of operation, together with further objectives and advantages, may be best understood by reference to the following description, taken in connection with the accompanying drawings, which are described below.

DETAILED DESCRIPTION OF EXEMPLARY EMBODIMENTS

The exemplary embodiments of the valve system and methods of use disclosed are discussed in terms of medical systems inserted with a body of a subject for the administration of fluids, and more particularly, in terms of a valve system, having multiple ports, which is manipulated to establish fluid communication with a passageway of a nasogastric tube to avoid leakage of intestinal fluids and minimize disease propagation. It is envisioned that the present disclosure finds application for the removal of fluids from a body of the subject, such as aspirating fluids from the body or to introduce nutrients, supplements, medicines, etc. to the body. It is further envisioned that the valve system may be used with nasogastric tubing to decompress the contents of the subject's stomach and facilitate removal of accumulated fluids, blood, etc. from the GI tract due to disease, intestinal obstruction, bleeding ulcers and paralytic ulcers. It is contemplated that the valve system may be used with nasogastric tubing for abdominal surgery to keep the stomach vacant of fluid and postoperatively to prevent complications, such as, decreased gastrointestinal function. It is further contemplated that the valve system finds application in protecting gastric suture lines, preventing and treating paralytic ileus, treating drug overdoses, lavage, as well as other conditions that affect the GI tract. A practitioner may employ such a valve system in hospitals, nursing homes, care facilities, etc.

In the discussion that follows, the term "proximal" will refer to the portion of a structure that is closer to a practitioner, while the term "distal" will refer to the portion that is further from the practitioner. As used herein, the term "subject" refers to a human patient or other animal having fluids administered therewith, including removal and introduction as discussed herein. According to the present disclosure, the term "practitioner" refers to a doctor, nurse, or other care provider utilizing the valve system with medical tubing, and may include support personnel.

Reference will now be made in detail to the exemplary embodiments of the present disclosure, which are illustrated in the accompanying figures. Turning now to the figures wherein like components are designated by like reference numerals throughout the several views and initially to FIGS. 1 and 2, there is illustrated a nasogastric valve system 20, in accordance with the principles of the present disclosure.

Nasogastric valve system 20 includes a valve connector 22 that defines a longitudinal axis x and includes a second portion 24 of a first passageway 26. Valve connector 22 further includes a suction port 28 and an introduction port 30 that are spaced apart and in substantially parallel alignment. Suction port 28 and introduction port 30 are manipulable to establish fluid communication between portion 24 of first passageway 26 and suction port 28 or introduction port 30. This configuration advantageously avoids leakage of intestinal fluids and minimizes disease propagation, as will be discussed herein.

The component portions of valve connector 22, which may be disposable, are fabricated from materials suitable for nasogastric tubing applications for the administration of fluids with a subject including removal and introduction. These materials may include suitable medical grade, flexible, semi-rigid and rigid plastic materials, which may incorporate polyvinylchloride (PVC), silicone, etc., as well as medical grade metals, such as stainless steel and aluminum, depending on the particular nasogastric tubing application and/or preference of a practitioner. One skilled in the art, however, will realize that other materials and fabrication methods suitable for assembly and manufacture, in accordance with the present disclosure, also would be appropriate.

Nasogastric valve system 20 includes a flexible nasogastric tube 32 that has a fluid lumen 34 and a vent lumen 36. Fluid lumen 34 and vent lumen 36 are disposed in a side-by-side, parallel relationship and extend from a proximal end 37 to a distal end 44 of nasogastric tube 32. It is contemplated that nasogastric tube 32 may be monolithically formed or, alternatively, fluid lumen 34 and vent lumen 36 may be separately formed and integrally joined thereafter. It is further contemplated that fluid lumen 34 and vent lumen 36 may not be attached.

Fluid lumen 34 is configured to aspirate fluids from a GI tract of the subject (not shown) or to introduce nutrients, supplements, medicines, etc. to the subject. Vent lumen 36 is configured to regulate the amount of suction and flow during aspiration.

The component portions of nasogastric tube 32, which may be disposable, are fabricated from materials suitable for nasogastric tubing applications for the administration of fluids with a subject including removal and introduction. These materials may include suitable medical grade, flexible and semi-rigid plastic materials, which may incorporate polyvinylchloride (PVC), silicone, etc., as well as medical grade flexible metal structure, depending on the particular nasogastric tubing application and/or preference of a practitioner. One skilled in the art, however, will realize that other materials and fabrication methods suitable for assembly and manufacture, in accordance with the present disclosure, also would be appropriate.

Fluid lumen 34 defines a first portion 38 of first passageway 26. Vent lumen 36 defines a first portion 40 of a second passageway 42. First passageway 26 and second passageway 42 fluidly communicate adjacent a distal end 44 of nasogastric tube 32. It is envisioned that first passageway 26 and second passageway 42 do not fluidly communicate apart from distal end 44. Alternatively, first passageway 26 and second passageway 42 may fluidly communicate within valve connector 22 via appropriate structure, such as, for example, a connecting cavity, opening, etc. that facilitates communication therebetween.

Figure 3:
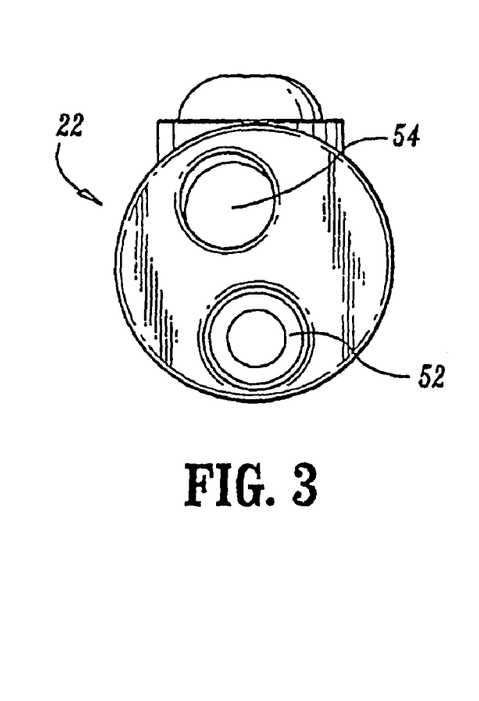
FIG. 3 is a front view of a distal end of a valve of the valve system shown in FIG. 1.

Valve connector 22 has a first end, such as, for example, proximal end 46 and a second end, such as, for example distal end 48. Referring to FIG. 3, distal end 48 includes a fluid port 52 and a vent port 54. Distal end 48 is attached to proximal end 37 of nasogastric tube 32 such that fluid port 52 and vent port 54 are received by fluid lumen 34 and vent lumen 36, respectively. Fluid port 52 and vent port 54 slidably engage respective interior surfaces of fluid lumen 34 and vent lumen 36 in a frictional interference fit to maintain a fluid sealing engagement between valve connector 22 and nasogastric tube 32. Valve connector 22 includes second portion 24 of first passageway 26 and a second portion 50 of second passageway 42.

Referring to FIGS. 4-7, valve connector 22 has a rotatable cylindrical outer cap 56 that includes suction port 28 and introduction port 30. Cap 56 is configured to facilitate manipulation of suction port 28 and introduction port 30 for establishing fluid communication with second portion 24 of first passageway 26. Cap 56 may have various cross-sectional configurations such as, for example, rectangular, polygonal, etc. to facilitate manipulation thereof. It is envisioned that cap 56 may be variably dimensioned with regard to, for example, diameter, length, etc. according to the requirements of a particular application.

Figures 1, 2:
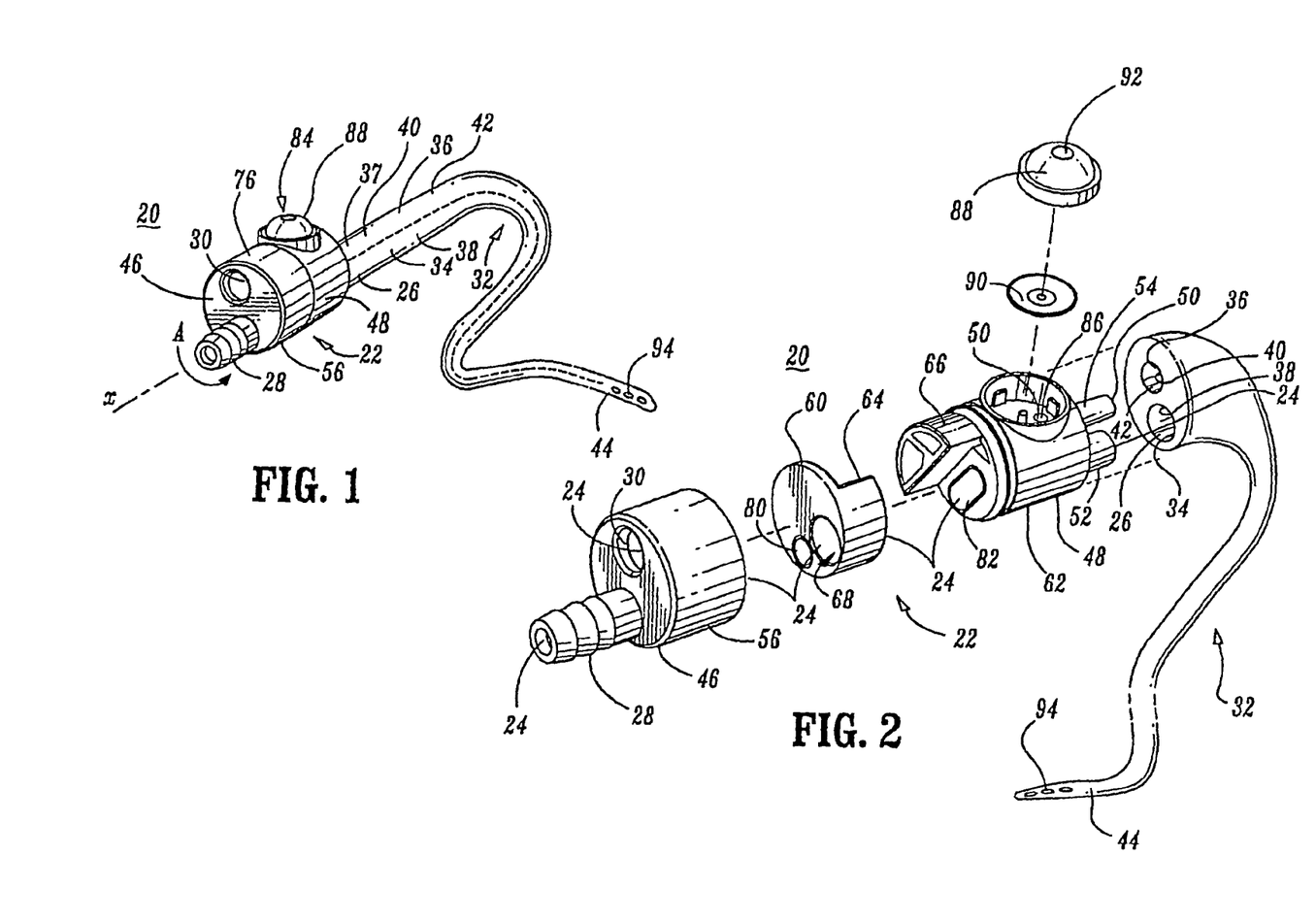
FIG. 1 is a perspective view of one embodiment of a valve system, in accordance with the principles of the present disclosure.
FIG. 2 is a perspective view of the valve system shown in FIG. 1, with parts separated.

Cap 56 is manually rotated by the practitioner, in the direction shown by arrow A (counter clockwise) in FIG. 1, to establish fluid communication between suction port 28 and first passageway 26 for aspirating fluids through fluid lumen 34. Alternatively, cap 56 is manually rotated by the practitioner, in the direction shown by arrow B (clockwise) in FIG. 11, to establish fluid communication between introduction port 30 and first passageway 26 for introducing nutrients, supplements, medicines, etc. to the subject. Cap 56 is rotatable through an angle of approximately 120 degrees to alternate fluid communication from suction port 28 to introduction port 30.

It is contemplated that cap 56 may be rotated clockwise and counter clockwise, in varying degrees of rotation through an angle up to and including 360 degrees, to establish fluid communication between suction port 28 or introduction port 30 and first passageway 26. It is further contemplated that cap 56 may be manipulated axially, angularly rotated relative to longitudinal axis x, etc. to establish fluid communication. It is envisioned that cap 56 may be rotated by mechanical, motorized, computerized, etc. devices to establish fluid communication with suction port 28 and introduction port 30, in accordance with the principles of the present disclosure.

Figures 4, 5:
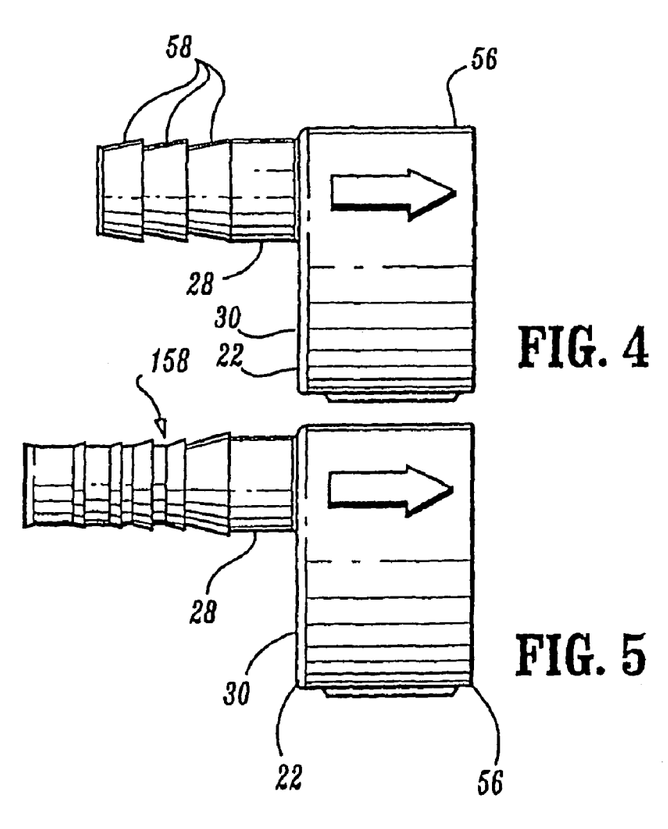
FIG. 4 is a cutaway side view of a proximal end of the valve shown in FIG. 1.
FIG. 5 is a cutaway side view of an alternate embodiment of the proximal end shown in FIG. 4.

Suction port 28 extends axially along longitudinal axis x and is configured for reception by suction tubing (not shown), which is connected to a source of suction (not shown), such as, for example, a vacuum pump, etc. Suction port 28 has a series of flanges 58, as shown in FIG. 4. Flanges 58 form a barb-like configuration to retain the suction tubing therewith. It is contemplated that the series of flanges 58 may be arranged in diameters that are uniform, increasing, decreasing, etc. to facilitate retention, according to the particular application. As shown in FIG. 5, an alternate embodiment of suction port 28 is shown, which includes flanges 158 that are arranged in an order of decreasing diameter.

Figures 6, 8:
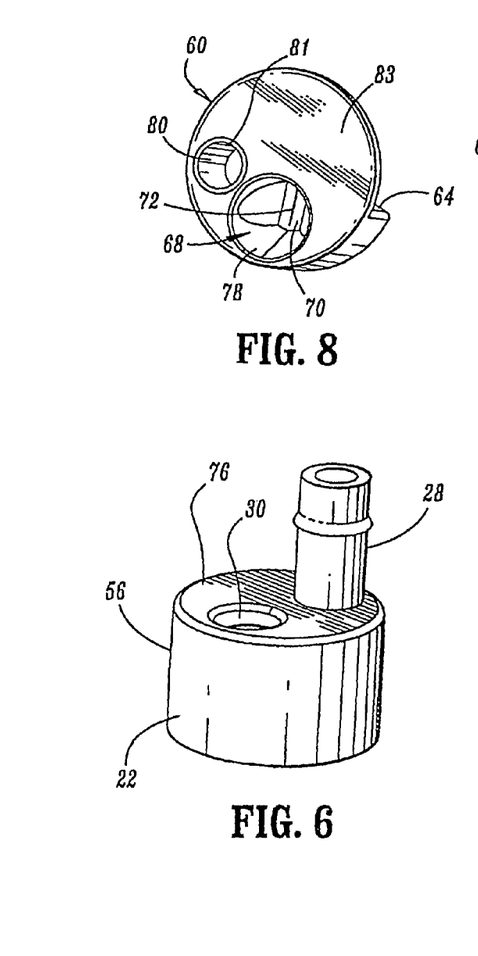
FIG. 6 is a side perspective view of a cap of the valve shown in FIG. 1.
FIG. 8 is a top perspective view of a part of the valve shown in FIG. 1.
Figure 7:
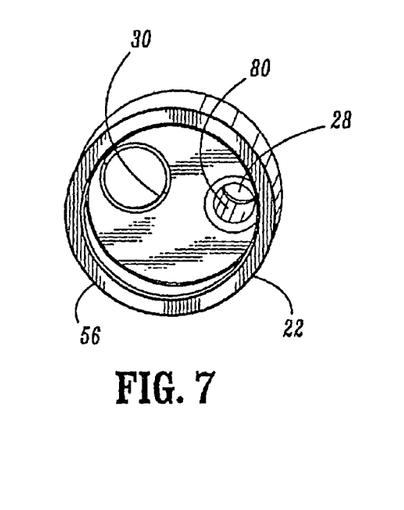
FIG. 7 is a bottom perspective of the cap shown in FIG. 6.
Figure 9:
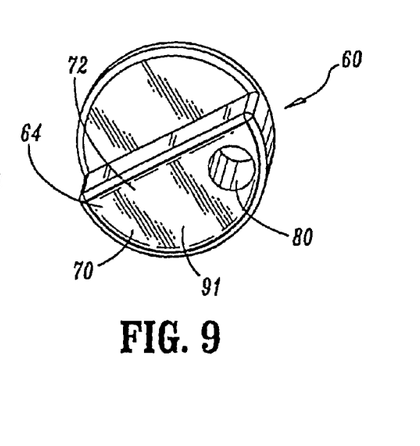
FIG. 9 is a bottom perspective view of the part shown in FIG. 8.
Figure 10:
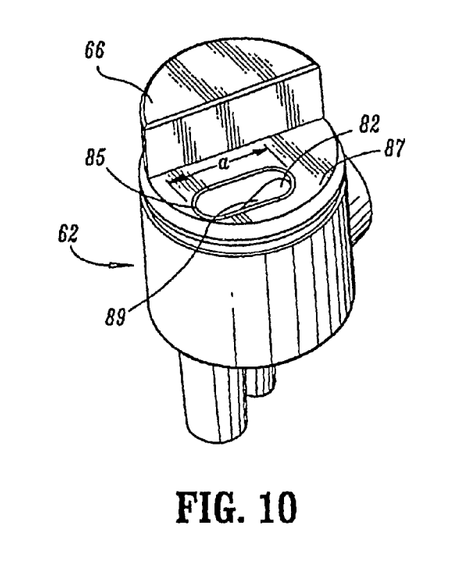
FIG. 10 is a perspective view of a body of the valve shown in FIG. 1.

Referring to FIGS. 8-10, valve connector 22 includes a part 60 and a body 62. Part 60 is disposed within cap 56 and has a stepped portion 64 that is configured to engage and fit with a correspondingly configured stepped portion 66 of body 62. Part 60 is fabricated from an elastomeric material such as, for example, rubber, etc. and configured to facilitate manipulation of cap 56 to establish fluid communication between suction port 28 or introduction port 30 and first passageway 26. Cap 56 rotates relative to part 60 to align suction port 28 or introduction port 30 with first passageway 26 as desired, and will be discussed further below. The elastomeric material of part 60 enables sealing of first passageway 26 during fluid communication. It is envisioned that part 60 may be fabricated from less flexible plastics or suitable metals.

Introduction port 30 includes a normally closed valve 68 that is formed in part 60. Normally closed valve 68 includes an elastically deformable septum 70 having an elongate slit 72 formed through a thickness of septum 70. It is contemplated that all or only portions of septum 70 may be elastically deformable.

Figure 12:
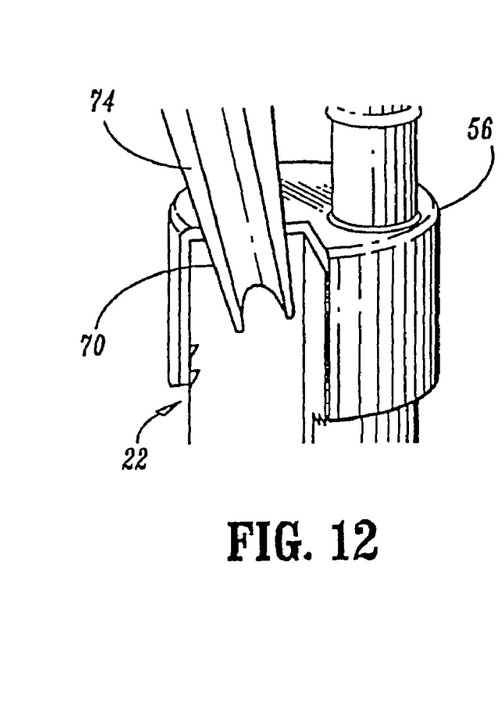
FIG. 12 is a cutaway perspective view of the valve system shown in FIG. 11 having a cannula inserted therewith.

Septum 70 is elastically deformable such that a cannula 74 (FIG. 12) is engageable with elongate slit 72 to establish fluid communication between cannula 74 and first passageway 26 for introducing nutrients, supplements medicines, etc. to the subject. Septum 70 has an angular orientation relative to longitudinal axis x to facilitate passing cannula 74 through slit 72. It is envisioned that septum 70 may be oriented at various angular orientations relative to longitudinal axis x, such as, for example, acute, perpendicular, etc. A feeding pump or the like may be introduced with introduction port 30 via septum 70 for constant or intermittent feeding of the subject.

Septum 70 is recessed relative to an outer surface 76 of valve connector 22. Valve connector 22 and normally closed valve 68 cooperate to define a recessed cylindrical cavity 78. It is contemplated that valve connector 22 or normally closed valve 68 may individually define cavity 78. Cavity 78 includes septum 70.

Part 60 includes a suction opening 80. Suction opening 80 facilitates communication between suction port 28 and first passageway 26. A raised lip 81 is circumferentially disposed, on a surface 83 of part 60, about suction opening 80. Surface 83 is configured for abutting engagement with the interior surface of cap 56 such that raised lip 81 facilitates sealing and prevents leakage of nasogastric valve system 20.

For example, cap 56 is manually rotated, in the direction shown by arrow A (counter clockwise) in FIG. 1, to establish fluid communication between suction port 28 and first passageway 26. Raised lip 81 is snug fit with the opening of suction port 28 in cap 56 to facilitate seating of cap 56 with part 60. This configuration prevents leakage from first passageway 26 during suction. It is contemplated that tactile feedback is provided to a practitioner via a snap, etc. fitting engagement of raised lip 81 with suction port 28, to indicate fluid communication is established between suction port 28 and first passageway 26. It is further contemplated that such tactile feedback indicates seating of suction port 28 with suction opening 80 and sealing of first passageway 26.

Figure 11:
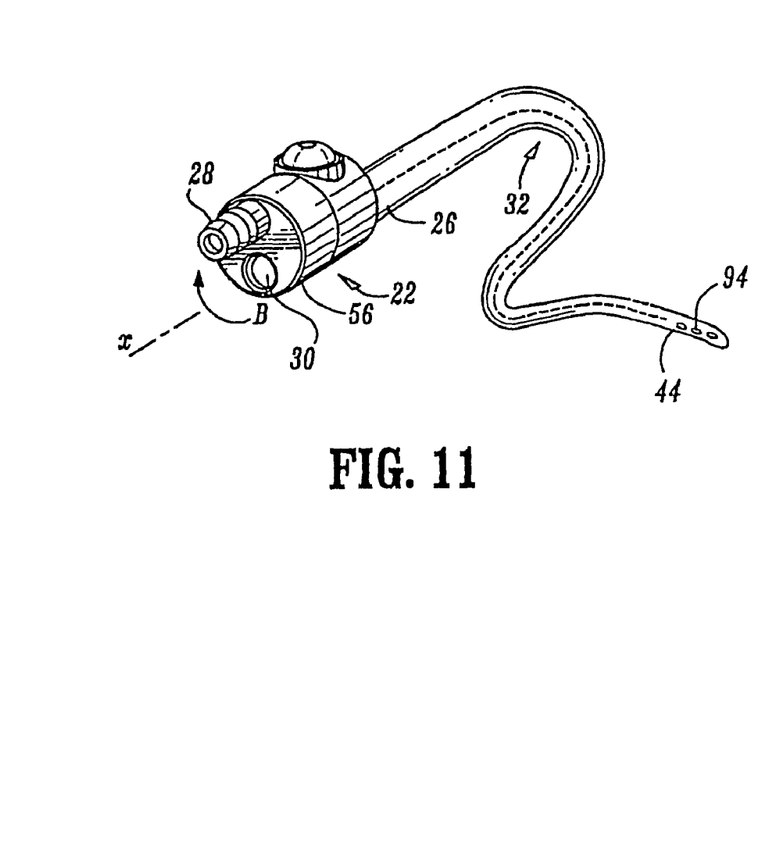
FIG. 11 is a perspective view of the valve system having the cap rotated for introduction.

Alternatively, cap 56 is manually rotated, in the direction shown by arrow B (clockwise) in FIG. 11, to establish fluid communication between introduction port 30 and first passageway 26. In this orientation, raised lip 81 engages the interior surface of cap 56 to seal off suction opening 80. This configuration prevents vacuum leakage from suction port 28 during fluid communication between introduction port 30 and first passageway 26. It is envisioned that raised lip 81 may have various geometries, thickness, height, etc. according to the requirements of a particular application. It is further envisioned that raised lip 81 may be variously disposed about suction opening 80 such as, for example, intermittent, undulating, etc.

Normally closed valve 68 is disposed adjacent to suction opening 80 for alignment with an angled flow path 82 of body 62. Flow path 82 has a width a of sufficient dimension such that suction opening 80 and normally closed valve 68 of part 60 are concurrently positioned into alignment therewith. This configuration advantageously facilitates establishing fluid communication with suction port 28 or introduction port 30 upon rotation of cap 56 relative to part 60. As suction opening 80 and normally closed valve 68 are in alignment with first passageway 26, suction port 28 or introduction port 30 can be manipulated, as desired for removing or introducing fluids to the subject. It is contemplated that suction port 28 and insertion port 30 are manipulable to establish fluid communication between first passageway 26 and suction port 28 and insertion port 30 concurrently.

A raised lip 85 is disposed, on a surface 87 of body 62, about an opening 89 of angled flow path 82. Surface 87 is configured for abutting engagement with a surface 91 of part 60 such that raised lip 85 facilitates sealing and prevents leakage of nasogastric valve system 20. Raised lip 85 engages surface 91 to prevent leakage from first passageway 26 during use. It is envisioned that raised lip 85 may have various geometries, thickness, height, etc. according to the requirements of a particular application. It is further envisioned that raised lip 85 may be variously disposed about angled flow path 82 such as, for example, intermittent, undulating, etc.

Referring back to FIGS. 1 and 2, second portion 50 of second passageway 42 includes a relief port 84. Relief port 84 is disposed with valve connector 22 and protrudes from outer surface 76. Relief port 84 includes an opening 86 that communicates with second passageway 42 and vent lumen 36. Vent lumen 36, second passageway 42 and relief port 84 are configured to regulate the amount of suction and flow during aspiration. It is contemplated that relief port 84 may be employed to clear nasogastric tube 32. A cap 88 and valve 90 are mounted with relief port 84. Cap 88 defines an opening 92 that is configured to receive a cannula (not shown) or the like, which communicates with vent lumen 36. It is contemplated that relief port 84 may be connected to atmospheric air, venting source, etc. It is further contemplated that cap 88 may include a one-way valve, bi-directional valve, etc.

In operation, a valve system 20, similar to that described in accordance with the principles of the present disclosure is provided for administration of fluids with a subject. The components of valve system 20 including valve connector 22 and nasogastric tube 32, similar to those described, are fabricated, properly sterilized and otherwise prepared for storage, shipment and use. Nasogastric tube 32 is manipulated such that fluid lumen 34 and vent lumen 36 receive fluid port 52 and vent port 54, respectively, as discussed. Thus, nasogastric tube 32 is attached to valve connector 22 so that second portion 24 and first portion 38 of first passageway 26 fluidly communicate. Second portion 50 and first portion 40 of second passageway 42 also fluidly communicate.

A practitioner introduces distal end 44 of nasogastric tube 32 through a nasal canal of a subject (not shown) via one of the nostrils. Distal end 44 is passed through the pharynx and down the esophagus into the GI tract. Distal end 44 can be passed into the duodenum, stomach, etc. depending on the particular application such as, for example, aspirating fluids, introduction for medication, feeding, etc. Several openings 94 are formed in distal end 44 that permit passage of gastric fluids, nutrients, medication, etc.

Cap 56 is rotated such that suction port 28 and introduction port 30 are manipulated to establish fluid communication between second portion 24 of first passageway 26 and suction port 28 or introduction port 30, as desired. Referring to FIG. 1, cap 56 is manually rotated by the practitioner, in the direction shown by arrow A (counter clockwise), to establish fluid communication between suction port 28 and first passageway 26 for aspirating fluids through fluid lumen 34 from the body of the subject. Raised lip 81 snugly fits with the opening of suction port 28 in cap 56, as described, providing tactile feedback to the practitioner that fluid communication is established and first passageway 26 is sealed. Valve system 20 may be connected to a collection vessel or the like to retain collected fluids.

Referring to FIG. 11, alternatively, cap 56 is manually rotated by the practitioner, in the direction shown by arrow B (clockwise), to establish fluid communication between introduction port 30 and first passageway 26 for injecting fluids. Raised lip 81 engages the interior surface of cap 56 to seal off suction opening 80, as described. In one embodiment, cannula 74 is inserted with normally closed valve 68, as discussed, to introduce nutrients, supplements, medicines, etc. to the body of the subject. Valve system 20 may be connected to a feeding pump or the like to provide constant or intermittent feeding. This configuration advantageously avoids leakage of intestinal fluids and minimizes disease propagation.

It is contemplated that nasogastric valve system 20 includes the necessary electronics and/or processing components to perform fluid measurement and analysis to facilitate diagnosis, treatment, etc. of a subject, as is known to one skilled in the art.

Figure 13:
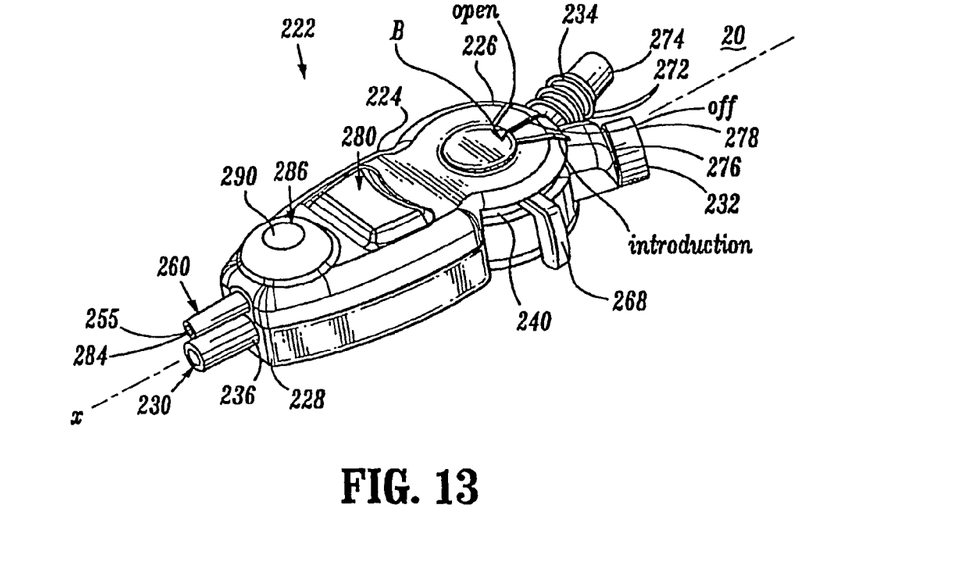
FIG. 13 is a perspective view of an alternate embodiment of the valve system, in accordance with the principles of the present disclosure.
Figure 14:
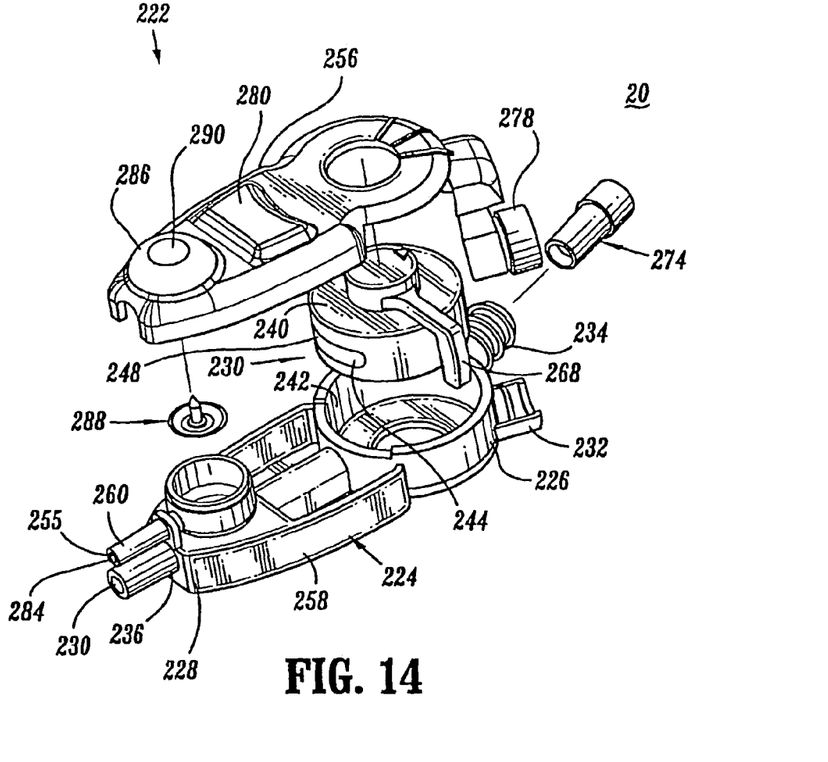
FIG. 14 is a perspective view of the valve system shown in FIG. 13, with parts separated.
Figures 15, 20:
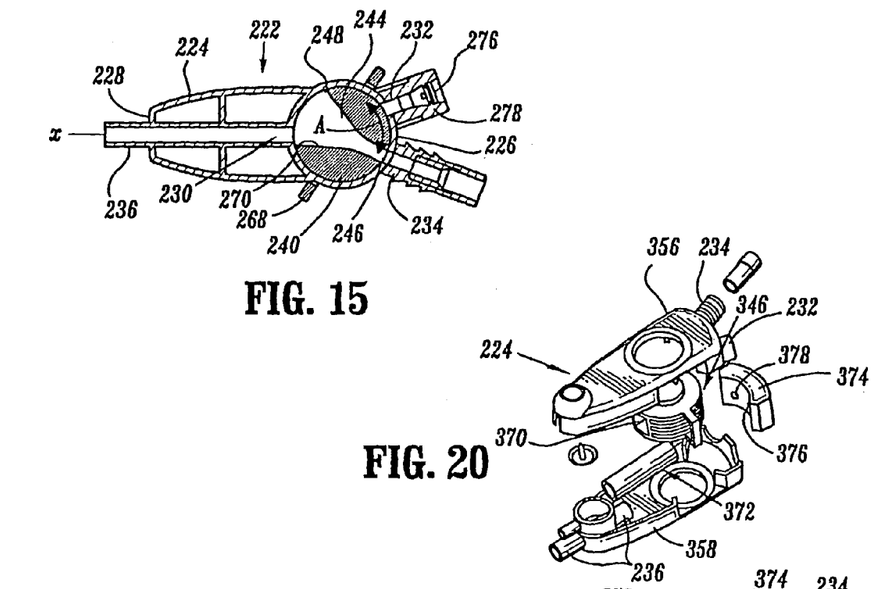
FIG. 15 is a top cross-sectional view of the valve system shown in FIG. 13.
FIG. 20 is a perspective view of the valve system shown in FIG. 19, with parts separated.
Figures 17, 18:
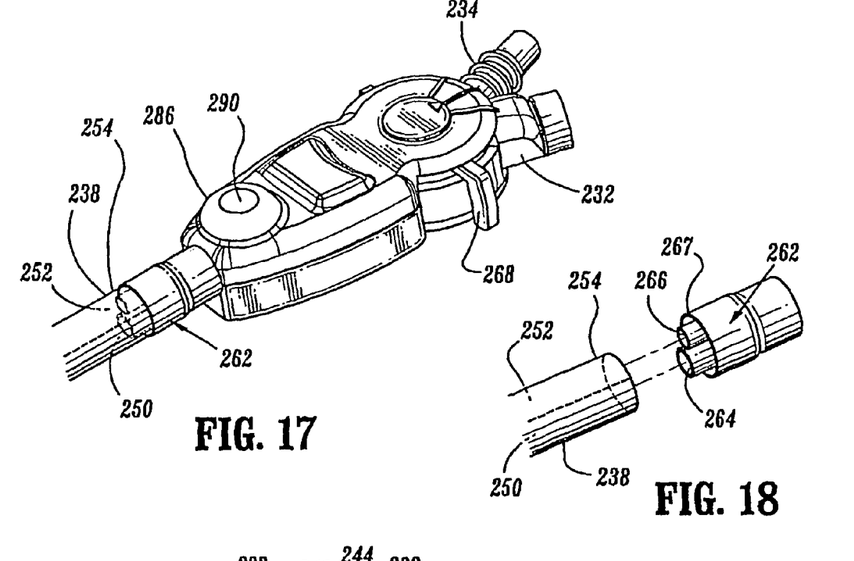
FIG. 17 is a perspective view of the valve system shown in FIG. 13 including a nasogastric tube.
FIG. 18 is a perspective cutaway view of a portion of the nasogastric tube and an adapter shown in FIG. 17.

Referring to FIGS. 13-15, an alternate embodiment of nasogastric valve system 20, similar to that described above, is shown that includes a valve 222. Valve 222 includes a housing 224 that defines a first end 226 and a second end 228. Housing 224 also defines a longitudinal axis x and includes a first passageway 230 that extends therealong. Housing 224 includes a first port, such as, for example, introduction port 232 and a second port, such as, for example, suction port 234. Introduction port 232 and suction port 234 are disposed adjacent first end 226. It is contemplated that ports 232, 234 may be in parallel alignment, offset, angularly disposed, etc. Housing 224 further includes a third port, such as, for example, an attachment port 236 disposed adjacent second end 228. Attachment port 236 facilitates connection to a nasogastric tube 238 (FIG. 17). First passageway 230 may have for example, a singular, branched, etc. configuration.

A valve member 240 is mounted for rotation within a cavity 242 of housing 224 relative to longitudinal axis x. Valve member 240 defines a portion 244 of first passageway 230 that includes a first opening 246 configured for alignment and sealed fluid communication with introduction port 232, in a first position, as will be discussed. First opening 246 is also configured for alignment and sealed communication with suction port 234, in a second position.

Portion 244 includes a second opening 248 having a greater relative dimension, as will be discussed, than first opening 246 and is configured to establish continuous fluid communication with first passageway 230. Valve member 240 is rotatable to establish sealed fluid communication between first opening 246 and introduction port 232, or alternatively, suction port 234, while maintaining a continuous sealed fluid communication between second opening 248 and attachment port 236. This configuration advantageously avoids leakage of intestinal fluids and minimizes disease propagation, as will be discussed herein.

Nasogastric valve system 20 includes flexible nasogastric tube 238 (FIGS. 17 and 18), similar to that described with regard to FIGS. 1-12, that has a fluid lumen 250 and a vent lumen 252. Fluid lumen 250 and vent lumen 252 are disposed in a side-by-side, parallel relationship and extend from a proximal end 254 to a distal end. Fluid lumen 250 defines a first portion of first passageway 230. Vent lumen 252 defines a portion of a second passageway 255. First passageway 230 and second passageway 255 fluidly communicate adjacent a distal end of nasogastric tube 238, similar to that shown in FIG. 2.

Housing 224 has a first section, such as, for example, top 256 and a second section, such as, for example bottom 258. Top 256 and bottom 258 are assembled together to enclose the components of valve 222. Top 256 and bottom 258 are ultrasonically bonded together, however, may be alternatively assembled employing adhesive, clips, etc.

An adapter 262 (FIG. 18) includes a fluid lumen 264 and a vent lumen 266 that are bonded to fluid lumen 250 and vent lumen 252 of nasogastric tube 238, as shown in FIG. 17, to provide a sealed fluid communication between valve 222 and tube 238. Adapter 262 facilitates connection of tube 238 and valve 222 and is configured such that a user can easily remove tube 238 from valve 222 for maintenance and replacement. Adapter 262 is bonded to tube 238 and includes a surface 267 at its periphery that bonds to the outer surface of tube 238 to provide strain relief. Adapter 262 may be ultrasonically bonded, adhered, monolithically formed with, etc. to nasogastric tube 238. Adapter 262 may be fabricated from a soft, semi-rigid or rigid material and include an oversized geometry, surface texturing, ribbing or additional material to enhance gripping and manipulation thereof.

Second end 228 includes attachment port 236 and a vent port 260. Second end 228 is attached to adapter 262 such that attachment port 236 and vent port 260 are received by fluid lumen 264 and vent lumen 266, respectively. Attachment port 236 and vent port 260 slidably engage respective interior surfaces of fluid lumen 264 and vent lumen 266, facilitating corresponding fluid communication with lumens 250, 252, respectively, in a frictional interference fit to maintain a fluid sealing engagement between valve 222 and nasogastric tube 238.

Valve member 240 is mounted within cavity 242 for rotation of first opening 246 to a plurality of positions. Valve member 240 includes a handle, such as, for example, selection knob 268 for manipulation thereof and to facilitate rotation of first opening 246, as shown by arrow A in FIG. 15, in a clockwise and counter-clockwise direction relative to longitudinal axis x. Selection knob 268 may be manipulated to rotate opening 246 into a first position, such as, for example, an open position (not shown).

In the open position, opening 246 is in alignment and sealed fluid communication with suction port 234. Indication to the user that opening 246 is in the open position is provided by visual indicia displayed from the outer surface of housing 224. The visual indicia includes a raised surface corresponding to the position of opening 246 and arrow B of valve member 240 that is directed to suction port 234. Alternative to the raised surface, depressions, mechanical detents, light emitting surface, etc. may be used. Valve 22 may also employ tactile and audible indicia, similar to the visual indicia used.

Opening 246 may be rotated into a second position, such as, for example, an introduction position (FIG. 15) such that opening 246 is in alignment and sealed fluid communication with introduction port 232. Indication to the user that opening 246 is in the introduction position is provided by visual indicia displayed from the outer surface of housing 224; Opening 246 may also be rotated into a third position, such as, for example, an off position (FIG. 1) such that opening 246 is not aligned with ports 232, 234 and fluid communication is prevented therebetween. Indication to the user that opening 246 is in the off position is provided by visual indicia displayed from the outer surface of housing 224.

Figure 19:
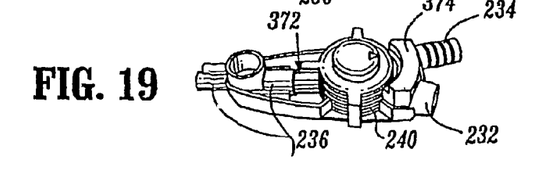
FIG. 19 is a perspective view of an alternate embodiment of the valve system shown in FIG. 13 with a housing section removed.

Valve member 240 has a solid core stopcock body including a bore 270 formed therethrough. Bore 270 flares from circular opening 246 to the wide oval configuration of second opening 248. This configuration advantageously accommodates rotation of valve member 240 while maintaining continuous sealed fluid communication between second opening 248 and first passageway 230 during manipulation of valve member 240. In an alternate embodiment as shown in FIGS. 19 and 20, valve member 240, mounted within a top 356 and a bottom 358 of a housing 324, defines a uniform bore 370. Tubing 372 is disposed within bore 370 for fluid communication with first passageway 230 and connects to attachment port 236. Tubing 372 extends to an opening 346 and is configured to facilitate continuous fluid communication with first passageway 230. Tubing 372 is flexible for rotation with valve member 240 to establish fluid communication with introduction port 232 and second port 234. A gasket 374, having openings 376 and 378 aligned with ports 232, 234 respectively, is mounted within housing 324 to facilitate fluid communication with first passageway 230. This configuration minimizes flow path volume and surface area.

Valve member 240 may have various configurations such as, for example, rectangular, polygonal, etc. to facilitate manipulation thereof. It is envisioned that valve member 240 may be variably dimensioned with regard to, for example, diameter, length, etc. according to the requirements of a particular application. Valve member 240 is fabricated from an elastometric material such as, for example, rubber, etc. and configured to facilitate manipulation thereof and establish fluid communication. Other semi-rigid and rigid materials are also contemplated.

It is contemplated that valve member 240 may be rotated clockwise and counter clockwise, in varying degrees of rotation through an angle up to and including 360 degrees, to establish fluid communication between ports 232, 234 and first passageway 230. It is further contemplated that valve member 240 may be manipulated axially, angularly rotated relative to longitudinal axis x, etc. to establish fluid communication. It is envisioned that valve member 240 may be rotated by mechanical, motorized, computerized, etc. devices to establish fluid communication with ports 232, 234, in accordance with the principles of the present disclosure.

Opening 246 is releasably locked in the open position, introduction position and off position via an anti-tamper mechanism of valve 222. The anti-tamper mechanism includes a blocking member (not shown) that is connected to a release button 280 and engages valve member 240 to fix opening 246 in alignment with introduction port 232 in the introduction position; suction port 234 in the open position; and out of alignment in the off position. Such engagement between blocking member 240 prevents rotation of knob 268 and is deactivated before knob 268 can be rotated. Release button 280 and the blocking member include such known structure necessary to effect blocking and release of valve member 240 such as, for example, spring loaded, cam arrangements, pivoting structure, etc.

Figure 16:
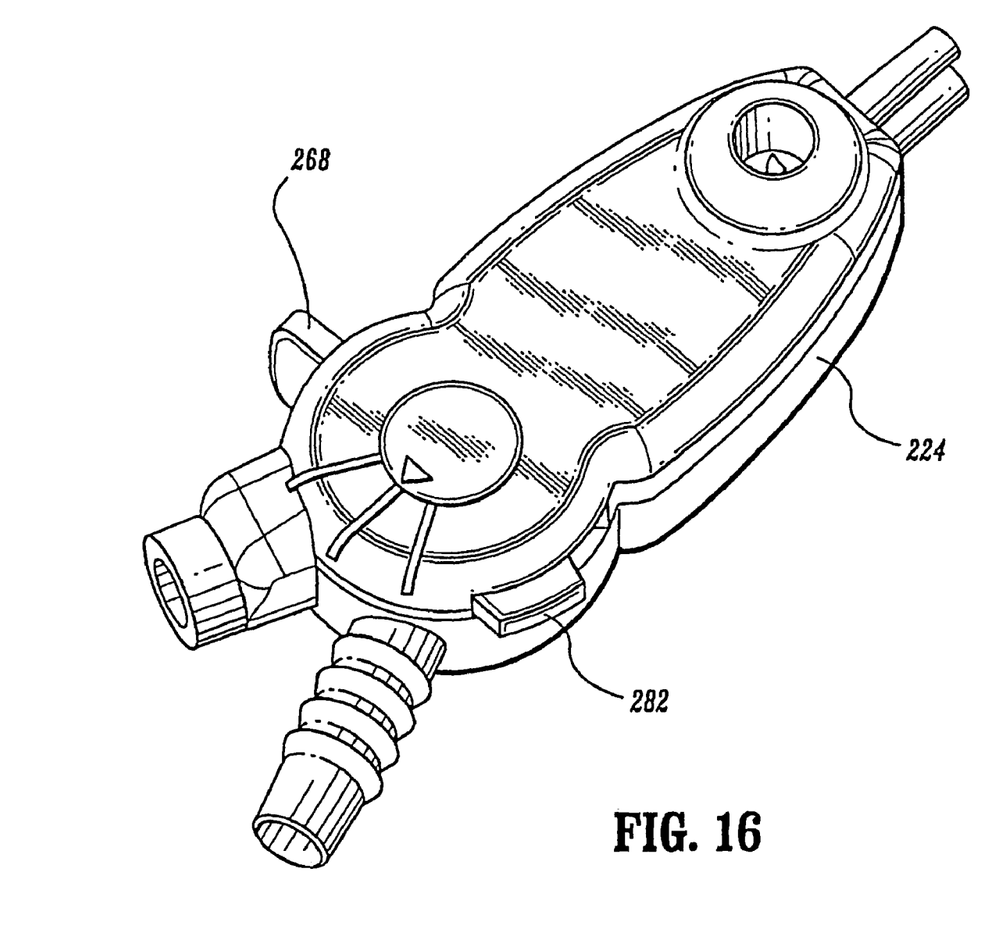
FIG. 16 is a perspective view of an alternate embodiment of the valve system shown in FIG. 13.

Housing 222 supports release button 280 that engages valve member 240 to release first opening 246 from alignment in a particular position. The practitioner depresses button 280 while manipulating knob 268. In an alternate embodiment, as shown in FIG. 16, an anti-tamper release button 282, similar to button 280 described, is disposed on a lateral portion of housing 224.

Suction port 234 extends at an angle slightly offset from longitudinal axis x and is configured for reception by suction tubing (not shown), which is connected to a source of suction (not shown), such as, for example, a vacuum pump, etc. Suction port 234 has a series of flanges 272 that form a barb-like configuration to retain the suction tubing therewith. It is contemplated that the series of flanges 272 may be arranged in diameters that are uniform, increasing, decreasing, etc. to facilitate retention, according to the particular application. Flanges 272 may be arranged in an order of decreasing diameter. Suction port 234 may include an enteral adapter 274 when continuous feeding is required. Adapter 274 is bonded to suction port 234, and may alternatively be adhered, monolithically formed, etc.

Introduction port 232 includes a normally closed valve 276 that is formed in a valve adapter 278 bonded to port 232. Normally closed valve 276 includes an elastically deformable septum having an elongate slit formed through a thickness of the septum.

The septum is elastically deformable such that a cannula (not shown) is engageable therewith to establish fluid communication between the cannula and first passageway 230 for introducing nutrients, supplements, medicines, etc. to the subject. A feeding pump or the like may be introduced with introduction port 30 via the septum for constant or intermittent feeding of the subject.

Second passageway 255 includes relief port 260. Relief port 260 includes an opening 284 that communicates with second passageway 255 and vent lumen 252. Vent lumen 252, second passageway 255 and relief port 260 are configured to regulate the amount of suction and flow during aspiration. It is contemplated that relief port 260 may be employed to clear nasogastric tube 238. An anti-reflux port 286 and anti-reflux valve 288 are mounted with housing 224 in fluid communication with relief port 260. Anti-reflux valve 288 prevents reflux from escaping through vent lumen 252 and regardless of the position of valve member 240, anti-reflux valve 288 is always operational.

Anti-reflux port 286 defines a membrane 290 that is configured to receive and permit passage of a cannula (not shown) or the like, for communicating with vent lumen 252. Anti-reflux port 286 allows the user to inject air into vent lumen 252 and establish a pressure activated buffer in vent lumen 252. It is contemplated that relief port 260 may be connected to atmospheric air, venting source, etc. It is further contemplated that cap 286 may include a one-way valve, bi-directional valve, etc.

In operation, a valve system 20, similar to that described with regard to FIGS. 13-20 in accordance with the principles of the present disclosure is provided for administration of fluids with a subject. The components of valve system 20 including valve 222 and nasogastric tube 238, similar to those described, are fabricated, properly sterilized and otherwise prepared for storage, shipment and use. Nasogastric tube 238 and adapter 262 are manipulated such that fluid lumen 264 and vent lumen 266 receive attachment port 236 and relief port 260, respectively, as discussed. Thus, nasogastric tube 238 is attached to valve 222 to establish fluid communication with first passageway 230 and second passageway 255.

A practitioner introduces the distal end of nasogastric tube 238 through a nasal canal of a subject (not shown) via one of the nostrils. The distal end of nasogastric tube 238 is passed through the pharynx and down the esophagus into the GI tract. The distal end of nasogastric tube 238 can be passed into the duodenum, stomach, etc. depending on the particular application such as, for example, aspirating fluids, introduction for medication, feeding, etc.

Knob 268 is manipulated for rotating opening 246 of valve member 240 to the open position, as confirmed by the visual indicia described above, to establish fluid communication between fluid lumen 250 and suction port 234. The open position setting facilitates suction through fluid lumen 250. Valve system 20 may be connected to a collection vessel or the like to retain collected fluids. Alternatively, an enteral feeding adapter 274 is attached to suction port 234 for continuous feeding.

When medication introduction to fluid lumen 250 is desired, release button 280 is deactivated before knob 268 can be manipulated to the introduction position, as described above. The user depresses and holds button 280 while manipulating knob 268. Knob 268 is manipulated to rotate opening 246 to introduction port 232 in a clockwise direction, as shown by arrow A, and confirmed by the visual indicia. The user releases button 280 to activate the blocking member and fix valve member 240 in the introduction position. An irrigation tip syringe (not shown) is introduced through normally closed valve 276 to administer medication, etc. through fluid lumen 250. Normally closed valve 276 automatically closes upon removal of the syringe to check backflow of contaminating gastric fluids. Valve system 20 may be connected to a feeding pump or the like to provide constant or intermittent feeding.

When patient transportation is desired, the user depresses and holds button 280 and manipulates knob 268 to rotate opening 246 to the off position, as confirmed by the visual indicia, in preparation for patient transportation. The user releases button 280 to activate the blocking member and fix valve member 240 in the off position. The configuration of valve system 20 advantageously avoids leakage of intestinal fluids and minimizes disease propagation.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A valve adapted for use with a nasogastric tube having a fluid lumen and a vent lumen, said valve comprising:
    a housing including therein a first passageway and a second passageway that includes a relief port, said first passageway being adapted for communication with the fluid lumen of said nasogastric tube and the relief port being adapted for communication with the vent lumen of the nasogastric tube, the housing further including a fluid introduction port and a fluid suction port;
    a valve member disposed within the housing and movable relative thereto, the valve member defining a portion of the first passageway that includes a first opening configured for alignment and sealed fluid communication with the fluid introduction port and the fluid suction port, the portion of the first passageway further including a second opening having a greater relative dimension than the first opening, wherein the valve member is manipulable to establish sealed fluid communication between the first opening and either the fluid introduction port or the fluid suction port while maintaining continuous sealed fluid communication between the second opening and the first passageway adjacent to the second end of the housing;
    an anti-reflux valve in the housing in fluid communication with the relief port, said anti-reflux valve being adapted to open to permit air to flow through the relief port when the first passageway and relief port are in communication with respective lumens of said nasogastric tube and suction is applied to the suction port; and
    wherein said second passageway is separate from the first passageway such that said valve member is not movable to any position establishing fluid communication between said first and second passageways.

2. A valve as recited in claim 1, wherein the valve member is disposed within the housing for rotation relative thereto to establish sealed fluid communication between the first opening and either the fluid introduction port or the fluid suction port.

3. A valve as recited in claim 1, wherein the valve member is manipulable to a position such that the first opening is not aligned with the fluid introduction port or the fluid suction port and fluid communication is prevented therebetween.

4. A valve as recited in claim 1, further comprising a handle connected to the valve member to facilitate manipulation thereof.

5. A valve as recited in claim 1, wherein the first opening is releasably lockable in alignment with the fluid introduction port or the fluid suction port.

6. A valve as recited in claim 5, wherein the housing supports a depressible button that engages the valve member to release the first opening from alignment with the fluid introduction port and the fluid suction port.

7. A valve as recited in claim 1, wherein the first port is configured for introduction of fluids into the first passageway.

8. A valve as recited in claim 1, wherein the fluid introduction port includes a normally closed valve.

9. A valve as recited in claim 8, wherein the normally closed valve includes an elastically deformable septum having an elongate slit formed through a thickness of the septum.

10. A valve as recited in claim 1, wherein the first passageway and a second passageway disposed within the housing fluidly communicate with a nasogastric tube.

11. A valve as recited in claim 1, wherein the housing further includes a third port that fluidly communicates with the first passageway and connects to tubing that extends to the second opening and is supported thereby, the tubing being configured to facilitate fluid communication of the first passageway with the fluid introduction port and the fluid suction port.

12. A valve as recited in claim 7, wherein the fluid suction port is configured for removal of fluids from the first passageway.

13. A valve as recited in claim 1 further comprising visual indicia on the housing indicating that the valve is in a fluid introduction position in which the first opening is aligned with the fluid introduction port and a fluid suction position in which the first opening is aligned with the fluid suction port.

14. A valve as recited in claim 4, wherein the handle is configured for one handed operation.

15. A valve as recited in claim 5, wherein the valve member supports a button that is engageable therewith to release the first opening from alignment with the fluid introduction port and the fluid suction port.

16. A valve as recited in claim 7, wherein the fluid suction port is configured for removal and introduction of fluids.

17. A valve as recited in claim 13, wherein the position of the valve member is confirmed by the visual indicia including a mechanical detent.

18. A valve as recited in claim 10, further comprising an adapter disposed for connecting the valve with the nasogastric tube and providing a sealed fluid communication therebetween.

19. A valve as recited in claim 18, wherein the adapter includes a surface adjacent its periphery that bonds to an outer surface of the nasogastric tube to provide strain relief.

20. A valve as recited in claim 18, wherein the adapter has an outer surface configured for enhanced manipulation thereof.

21. A valve as recited in claim 1 wherein the fluid introduction and suction ports are located adjacent a first end of the housing and the relief port is located adjacent a second end of the housing.

22. A valve as recited in claim 1 wherein the housing further comprises an anti-reflux port defined by a membrane that is configured to permit passage of a cannula for communicating with the relief port.

23. A valve as set forth in claim 1 wherein the anti-reflux valve comprises an umbrella valve configured to open in response to suction applied to the suction port.

24. A nasogastric valve system comprising:
   a nasogastric tube including a fluid lumen and a vent lumen, the fluid lumen defining a first portion of a first passageway, the vent lumen defining a first portion of a second passageway, wherein the first passageway and the second passageway fluidly communicate adjacent a distal end of the nasogastric tube;
   a housing defining a first end, a second end and a longitudinal axis, the housing including a second portion of the first passageway that extends therewithin and a second portion of the second passageway that extends therewithin and includes a relief port, the housing including an introduction port and a suction port, said introduction and suction ports being disposed adjacent the first end of the housing, the housing further including an attachment port disposed adjacent the second end of the housing for attachment of the nasogastric tube to the housing;
   a valve member mounted for rotation within a cavity of the housing relative to the longitudinal axis, the valve member defining a portion of the first passageway that includes a first opening configured for alignment and sealed fluid communication with the introduction port, in a first position, and the suction port, in a second position, the portion of the first passageway further including a second opening having a greater relative dimension than the first opening and being configured to establish continuous fluid communication with the first passageway, wherein the valve member is rotatable to establish sealed fluid communication between the first opening and the introduction port or the suction port while maintaining continuous sealed fluid communication between the second opening and the attachment port; and
   an anti-reflux valve in the housing in fluid communication with the relief port, said anti-reflux valve being adapted to open to permit air to flow through the relief port when the first passageway and relief port are in communication with respective lumens of said nasogastric tube and suction is applied to the suction port; and
   wherein said second portion of the second passageway is separate from the second portion of the first passageway such that said valve member is not movable to any position establishing fluid communication between said second portions of the first and second passageways.

25. A valve system as recited in claim 24, wherein the housing comprises top and bottom clamshell sections assembled to enclose the valve member, and a handle disposed outside the housing for moving the valve member in the housing.

26. A valve system as set forth in clam 24 wherein the anti-reflux valve comprises an umbrella valve configured to open in response to suction applied to the suction port.

* * * * *